United States Patent le Parlouer et al.

[11] Patent Number: 6,062,727
[45] Date of Patent: May 16, 2000

[54] MEASURING INSTRUMENT FOR THE THERMAL AND/OR REACTIVE PROPERTIES OF ONE OR SEVERAL MATERIAL SAMPLES

[75] Inventors: Pierre le Parlouer; Jean-Louis Daudon, both of Caluire, France

[73] Assignee: Setaram - Societe d'Etudes d'Automatisation de Regulation et d'Appareils de Mesures, Caluire, France

[21] Appl. No.: 09/030,225

[22] Filed: Feb. 25, 1998

[30] Foreign Application Priority Data

Mar. 7, 1997 [FR] France .................................. 97 02959

[51] Int. Cl.⁷ .................................................. G01N 25/00
[52] U.S. Cl. ........................ 374/12; 422/85.12; 422/102; 374/45; 73/865
[58] Field of Search ................................. 73/865, 863.11, 73/866, 54.22, 25.01, 25.03; 374/45, 12, 11, 13; 422/102, 82.12

[56] References Cited

U.S. PATENT DOCUMENTS

| | | | |
|---|---|---|---|
| 4,117,712 | 10/1978 | Hager, Jr. | .................................... 374/9 |
| 4,303,615 | 12/1981 | Jarmell et al. | .......................... 422/102 |
| 4,456,919 | 6/1984 | Tomita et al. | .......................... 357/284 |
| 4,906,105 | 3/1990 | Geake | ....................................... 374/30 |
| 5,520,866 | 5/1996 | Bennett et al. | .......................... 422/102 |

FOREIGN PATENT DOCUMENTS

| | | |
|---|---|---|
| 41-978 | 2/1986 | Japan . |
| 42371 | 2/1990 | Japan . |
| WO9102229 | 2/1991 | WIPO . |

*Primary Examiner*—Thomas P. Noland
*Attorney, Agent, or Firm*—Dowell & Dowell, P.C.

[57] ABSTRACT

A measuring instrument for the thermal and/or reactive properties of one or several samples of a solid, liquid or gaseous substance, comprising a measuring cell constituted by an electronic component suitable to detect a temperature difference between two regions on it's surface. The instrument includes a thermal inertia block defining an inner chamber in which is contained the measuring cell and which block is provided with an opening above the measuring cell and a skirt surrounding the chamber. The skirt extends vertically downwardly to an essentially horizontal bearing surface.

12 Claims, 2 Drawing Sheets

MEASURING INSTRUMENT FOR THE THERMAL AND/OR REACTIVE PROPERTIES OF ONE OR SEVERAL MATERIAL SAMPLES

BACKGROUND OF THE INVENTION

1. Field of the Invention

The present invention relates to a measuring instrument for the thermal and/or reactive properties of one or several samples of material. The thermal and/or reactive properties of a material are materialized by a heat flow either entering or leaving the sample under given conditions.

2. Description of the Related Art

The hitherto known devices of such type are most frequently complex, heavy, voluminous instruments that must be exclusively used in laboratories because they cannot be easily moved and whose cost is high. Furthermore, the volume of the measuring chamber of these instruments and the reaction time of the cells used bring about a considerable thermal inertia of these devices, so that a high-quality isothermic chamber must be used. This, however, elevates the costs of these devices and increases their sizes.

Further, from the claims of patent WO 91/02229 is known a measuring cell for the temperature difference between two zones of its surface that is susceptible to be used in a measuring instrument for the thermal properties of a sample of material. A cell of such type, however, is fragile and cannot be used as is without risking that it be damaged because of the handling necessary for the placing and withdrawing of a sample. Furthermore, it must be connected to an electronic control circuit and it must be continue to be possible to tap and disconnect it, in particular, for a change of components or for preventive maintenance operations. This cell may operate in an open atmosphere but the measurements it takes at such time are false because of the perturbations due to the ambient atmosphere.

SUMMARY OF THE INVENTION

The present invention has the aim to solve all of these problems and to put forward a measuring instrument for the thermal and reactive properties of the samples of materials, using a cell of above-mentioned type and allowing its thermal insulation with respect to the outside atmosphere, its mechanical protection and, should it become necessary, access to it and to the electronic control or detection circuit. The present invention has also the aim to build a compact measuring instrument that is, in particular, moveable and autonomous, and suitable to be transported to the site where the measures are to be taken. This compact nature also brings about improved economic results.

With this in mind, the present invention relates to a measuring instrument for the thermal and reactive properties of one or of several samples of a solid, liquid or gaseous material, comprising a measuring cell, constituted by an electronic component suitable to detect a temperature difference between two zones of its surface, characterized by the fact that it comprises a thermal inertia block constituting an inner chamber in which is located the measuring cell. The block is provided with an opening above the measuring cell, with a skirt surrounding the chamber, which skirt extends vertically downwardly to an essentially horizontal bearing surface.

Thanks to the present invention, the measuring cell is shrouded by the thermal insulation block that protects it mechanically and insulates it thermically. The opening above the cell allows a sample of the substance whose thermal properties are to be measured to be placed on its upper surface.

In accordance with a first advantageous aspect of the present invention, the thermal inertia block is made out of a metal such as, for example, aluminum. The good machining properties, the relatively low density of this metal and its affordable cost make it possible to obtain a relatively light-weight block that would efficaciously ensure the desired function at a low cost price.

In accordance with another advantageous variant of the present invention, the instrument comprises an aperture shutter, which shutter is provided with a central insertion channel for the sample. Thus, a sample can be positioned while the shutter closes the opening, so that a direct access to the measuring cell is not possible, so that it is protected against any erroneous handling and so that no outside air flow can influence the measurement. On the other hand, when it becomes necessary to access the cell to clean it, the shutter can be removed from the opening and, by taking the necessary precautions, it is possible to work on the measuring cell.

In accordance with an advantageous embodiment of the present invention, the instrument comprises a tubular sleeve arranged on the measuring cell and which is suitable to house a crucible holding the sample. This contributes to an exact placing of the crucible holding the sample, in particular when such a sample is a liquid substance.

In accordance with another particularly advantageous aspect of the present invention, the instrument comprises at least one Peltier element located in the proximity of the measuring cell inside the inner chamber. The adjustment of the measuring cell temperature and/or of the chamber is obtained thanks to this Peltier element. This feature of the present invention makes it possible to adapt the measuring temperature to the total of the desired temperatures and, in particular, to conduct measurements on a predetermined range of temperatures.

In accordance with another advantageous aspect of the present invention, the measuring cell is supported by an elastic pull-back element in direction of the opening. This aspect of the invention allows an accurate positioning of the cell inside of the chamber, allowing, however, a certain degree of clearance for the cases of dilatation and ensuring a close thermal contact with an eventual temperature control element, such as the Peltier couple.

In accordance with another advantageous aspect of the present invention, the instrument comprises a solid element provided with fins constituting the heat exchange surface. Thus, it is possible to reduce the thermal inertia of the entire instrument. Therefore, this element's temperature remains close to the ambient temperature, whatever might be the thermal flow exchanged through this solid element, which allows an efficient control of the measuring cell within an ample temperature range. As a matter of fact, whichever might be the temperature at the level of the cell, the solid element constitutes a reference element whose temperature can be considered, at least approximately, as being constant.

In accordance with another advantageous aspect of the present invention, the horizontal bearing surface on which rests the thermal inertia block has at least one connecting opening between the inner chamber and the outside. This opening can be used to access the measuring cell and/or a therewith connected electronic control circuit.

In accordance with an advantageous variant of the invention, the cell is suitable to determine the mass or a variation thereof of the sample. This enables one to realize the scope of the sample's study.

BRIEF DESCRIPTION OF THE DRAWINGS

The invention will be better understood and some other of its advantages will be shown more clearly through the below description of two embodiments of a measuring instrument for the thermal properties of a sample of material in accordance with its principle, given only by way of example and making reference to the accompanying illustrations wherein.

DESCRIPTION OF THE PREFERRED EMBODIMENTS

Figure 1:
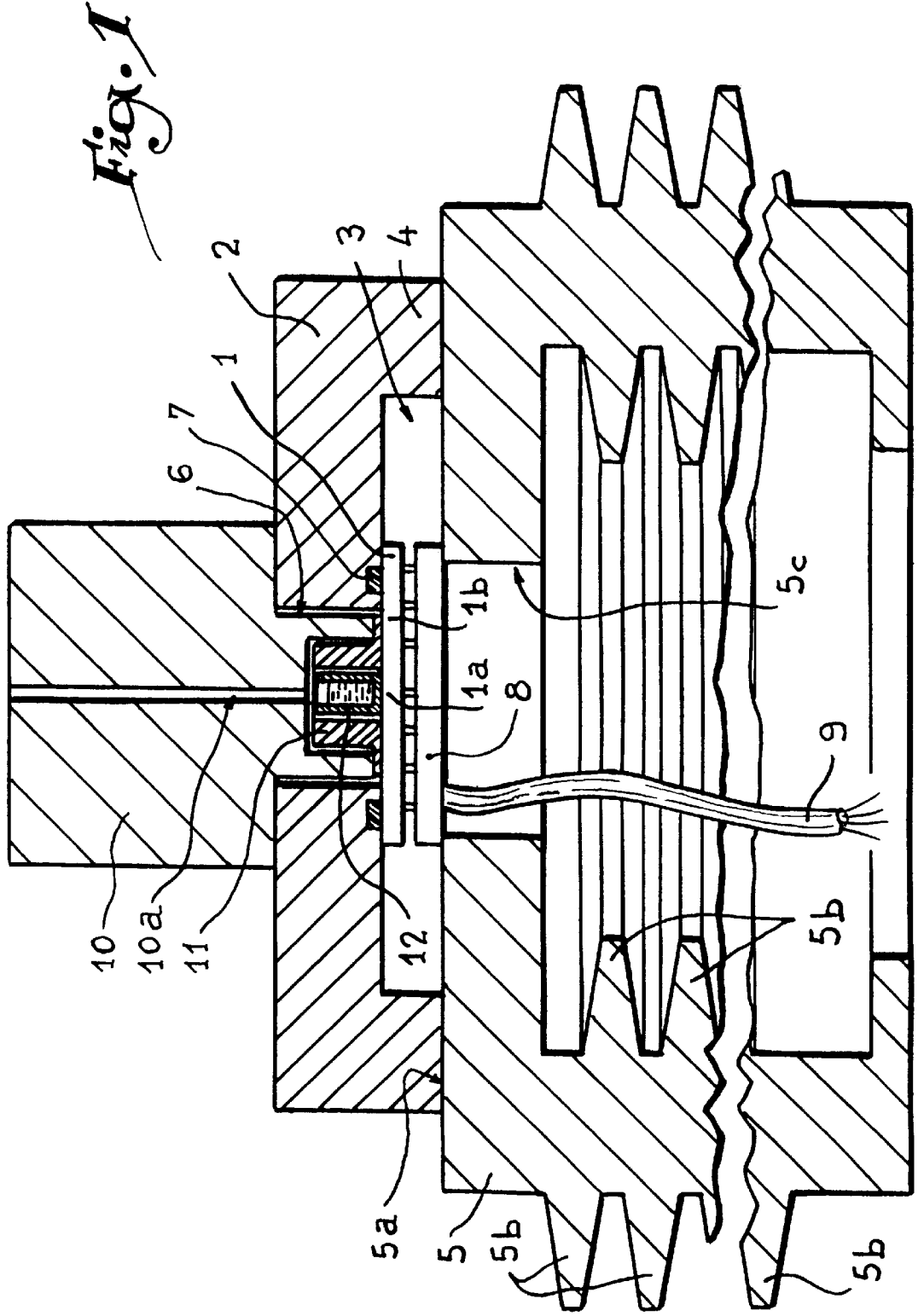
FIG. 1 is a cross-sectional view of a measuring instrument in accordance with a first embodiment of the present invention.

The instrument illustrated in FIG. 1 is comprised of a measuring cell 1, constituted by an electronic component, suitable to detect a temperature difference between its central region 1a and a peripheral region 1b. By way of example but not necessarily, the cell 1 can be of the type described in patent WO-A-91/02229. It can be a differential measuring cell, that is to say, symmetric or absolute, namely, asymmetrical.

In accordance with the present invention, the thermal inertia block 2 constitutes an inner chamber 3 in which is located the cell 1. The block 2 is provided with an external annular skirt 4 surrounding the chamber 3 and extending vertically downwards to an essentially horizontal bearing surface 5a belonging to a radiator 5 provided with heat exchange fins 5b. The block 2 is provided with an opening 6 above the cell 1. This opening renders it possible to access the upper surface of the cell 1. A joint 7, such as, for example, a toroidal joint, is set in an annular groove of one face of the block 2 in a direction towards the cell 1 and its function is that of insulating the chamber 3 from the opening 6 and, in particular, to impede the circulation of an air current from the chamber 3 towards the upper surface of the central region 1a of the cell 1.

The block 2 and the radiator 5 are made out of aluminum or out of another non-ferrous metal, which confers it good thermal properties and good machining at a relatively low cost. An electronic circuit 8 is connected to the cell 1 and serves for its power supply and to communicate with an indicator located on the outside. A cable bundle 9 passes through a communication opening 5c bored in the upper surface 5a of the radiator 5, which opening communicates with the chamber 3 and the ambient atmosphere.

The cell 1 is put into place before the block 2 is placed on the surface 5a. Should it become necessary to check the cell, the block 2 can be easily removed.

An obturator 10 is of such a size that it closes the opening 6 by resting on the block 2. This obturator is provided with a central channel 10a that allows the insertion of the sample of the material of which the thermal properties are to be measured while the obturator is in place. This makes it possible to take the measurements without a breakdown and by protecting the cell 1 against any erroneous handling. The sample can be inserted above the cell 1 through the channel 10a by means of a needle connected to a syringe or by any other similar means, such as a capillary tube.

A tubular sleeve 11 is mounted on the cell 1 and is suitable to house a crucible 12 in which is placed the sample of the substance.

The functioning is as follows: prior to conducting the measurement, the sleeve 11 and the crucible 12 are placed on the upper surface of the cell 1. Then, after the obturator 10 is placed, the sample of the substance to be analyzed is inserted in the crucible 12. After the measuring operations are concluded, the obturator 10 can be uncoupled in order to retrieve the crucible 12. It must be noted that thanks to the presence of the crucible 12, the upper surface of the measuring cell 1 is not dirtied by the sample of the product to be analyzed. Furthermore, the use of the sleeve 11 is not required, especially, if the geometry of the crucible 12 affords it a good positioning.

Figure 2:
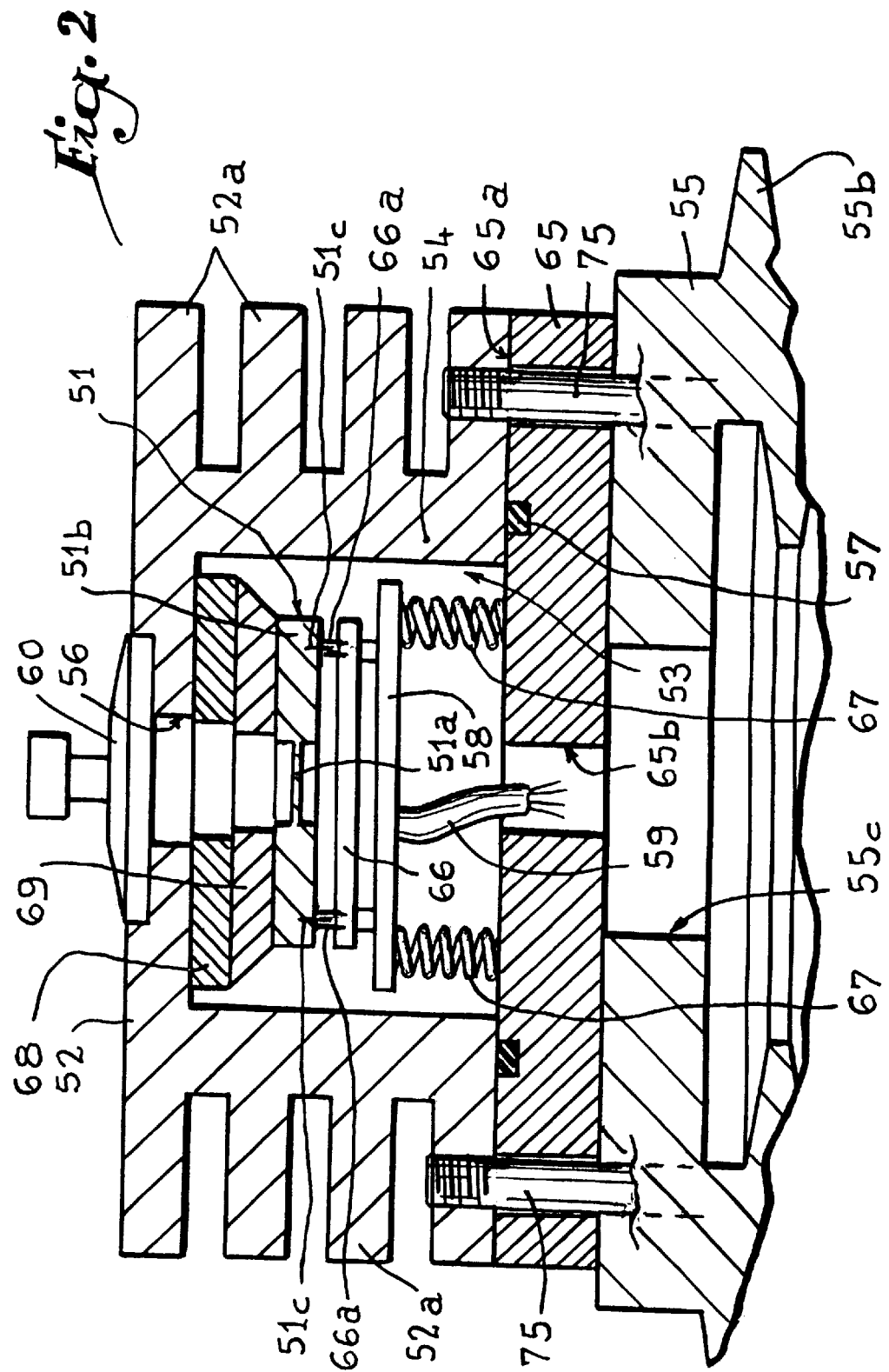
FIG. 2 is a view analogous to that of FIG. 1 of an instrument in accordance with a second embodiment of the present invention.

In the second embodiment of the present invention, illustrated in FIG. 2, the elements that are similar to those of the embodiment of FIG. 1 are referenced by the same numbers increased by 50. In this embodiment, a measuring cell 51, mounted inside a chamber 53 that is constituted by a thermal inertia block 52, is provided with an external annular skirt 54 that extends vertically downwards in the direction of an essentially horizontal bearing surface 65a of a plate 65 resting on a radiator 55 provided with fins 55b. The block 52 is also provided with fins 52a facilitating the heat exchanges with the ambient atmosphere.

By means of screws 75, the block 52 of the radiator 55 and of the plate 65 can be interlocked. This renders it possible to move the entire instrument in one block to, for instance, the location of the measurement. When one wishes to position the cell 51 or the therewith connected electronic devices or check the former or the latter, the screws 75 are unscrewed and the block 52 is removed from the plate 65.

The block 52 is provided with an opening 56 above the cell 51, with an obturator 60 suitable to close the opening 56. The cell 51 is connected to an electronic control circuit 58, with a support 66 being arranged between the cell 51 and the circuit 58. This support 66 is provided with connector sockets 66a suitable to interact with connector pins 51c belonging to the cell 51. As before, the cell 51 can measure a temperature difference between one central region 51a and a peripheral region 51b of its upper surface. Thanks to the present invention, the fragile cell 51 is efficaciously protected by the block 52 both from a thermal and a mechanical point of view.

Slightly compressed springs 67 are placed between the circuit 58 and the bearing surface 65a belonging to the plate 65 so that they constitute an elastic pull-back element of the circuit 58 and the elements that support it, in particular the cell 51, in a direction of the opening 56. Thanks to this aspect of the present invention, the cell 51 is permanently positioned near the opening 56. The function of the springs 67 could also be carried out by only one compression spring whose diameter would be roughly the same as the transversal dimension of the circuit 58, which spring would be placed between this circuit and the surface 65a.

The plate 65 is provided with bore holes, of which only 65b can be seen in FIG. 2, allowing the passing of a bundle of cables 59 between the chamber 53 and the outside, in conjunction with an opening 55c of the radiator 55.

In accordance with an advantageous aspect of the present invention, a Peltier element 68 is arranged in the chamber 53 in the proximity of the cell 51, allowing the temperature of the cell and/or of the chamber 53 to be adjusted depending on the requirements of the measurements under way. A block-thermostat 69 is advantageously sandwiched between the element 68 and the cell 51 in such a manner as to constitute a regulator that controls the electric supply to the Peltier element 68. It must be recalled that a Peltier element is an electronic component which, supplied with current, produces such a thermal effect that the temperature increases on one of its sides while the temperature decreases on the other side depending on the current direction. Thus, when at the option of the user and depending on the direction of the current with which it is supplied, this element can either heat or cool the cell 51 and/or the chamber 53. The element 68 is arranged in such a manner that it is in contact with the block 52, so that a direct heat exchange can take place between these two components and that, thanks to the fins 52*a*, the calories eventually generated or absorbed by the element 68 can be exchanged by the block 52 with the ambient temperature. Even if the block 52 is not provided with fins, it is indirect contact with the radiator 55 and the heat exchange can also take place through this radiator.

In accordance with a not ill embodiment of the present invention, the connector sockets of the cell 51 can be provided on its periphery and extend horizontally; the corresponding connector pins of the support 66 are horizontally provided. It is also possible to install a second element Peltier above the cell 51 which improves the thermal effectiveness and the response time of the instrument.

The two instruments illustrated have the advantage of being very compact, easy to move from place to place and of having a low power consumption, so that they can be used outside of the laboratory, in particular on the site where the measurements are to be taken. Thanks to the bundles 9 and 59, they can be connected to a control unit such as a laptop computer, which ensures ease of use.

Furthermore, taking into account the small masses involved and the fast response time of the cell that are used, the instrument can be used without having to be confined in an isothermic enclosure, which keeps it's cost at a very competitive level and makes it possible to be small.

In accordance with a non illustrated embodiment of the present invention, the design can be such that the opening 5*c* or 65*b* is obturated by a plug that allows the passage of the cable bundle 9 or 59. This plug enables to obtain the insulation of the chamber 3 or 53 with respect to the ambient atmosphere.

The instrument can be used irrespective of the nature of the material of which the thermal properties are measured, be it solid, liquid or gaseous. The instrument can also be used to simultaneously measure the properties of several samples arranged side by side on the cell.

In accordance with a not illustrated variant of the present invention, the measuring cell can be suitable to determine the mass or a variation of the mass of the sample. In fact, the mass of a sample is one of its reactive characteristics to the extent where it influences a physical-chemical reaction and where such a reaction can lead to the variation of this mass. The measurement of the mass can be conducted by any appropriate method and, in particular, as a measure of an energy used to balance a mechanical system supporting the cell.

What we claim is:

1. A measuring instrument for the thermal and/or reactive properties of at least one sample of a solid, liquid or gaseous substance, the instrument comprising; a measuring cell constituted by an electronic component adapted to detect a temperature difference between two regions of its surface, a thermal inertia block having an inner chamber in which is contained said measuring cell, said block being provided with an opening above said measuring cell, and a skirt surrounding said chamber, which skirt extends vertically downwardly to an essentially horizontal bearing surface.

2. A measuring instrument in accordance with claim 1 wherein said block is made out of a metal.

3. A measuring instrument in accordance with claim 2 wherein said block is formed of aluminum.

4. A measuring instrument in accordance with claim 1 including an obturator for said opening, said obturator being provided with a central channel for the insertion of the at least one sample.

5. A measuring instrument in accordance with claim 1 including a tubular sleeve mounted on said measuring cell and adapted to retain a crucible for supporting the at least one sample.

6. A measuring instrument in accordance with claim 1 including at least one Peltier element mounting in the proximity of said measuring cell and within said inner chamber.

7. A measuring instrument in accordance with claim 1 wherein said measuring cell is supported by an elastic pull-back element relative to the opening.

8. A measuring instrument in accordance with claim 7 wherein said elastic pull-back element is provided at least with one compression spring inserted between an electronic control connected to said measuring cell and supporting it, and said essentially horizontal bearing surface.

9. A measuring instrument in accordance with claim 1 further including a solid element provided with fins that constitute heat exchange surfaces, and said solid element being in heat exchange relationship with said thermal inertia block.

10. A measuring instrument in accordance with claim 1 wherein said bearing surface includes at least one hole communicating between the inner chamber and an area outside of said chamber.

11. A measuring instrument in accordance with claim 10 including a cable bundle of a power supply for said cell passing through said at least one hole.

12. A measuring instrument in accordance with claim 1 wherein said cell is adapted to determine mass or a variation of mass of the sample.

* * * * *